(12) United States Patent
Miura

(10) Patent No.: US 10,281,443 B2
(45) Date of Patent: May 7, 2019

(54) GAS DETECTION DEVICE

(71) Applicant: TOYOTA JIDOSHA KABUSHIKI KAISHA, Toyota-shi (JP)

(72) Inventor: Masanori Miura, Toyota (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 169 days.

(21) Appl. No.: 15/207,008

(22) Filed: Jul. 11, 2016

(65) Prior Publication Data

US 2017/0067868 A1 Mar. 9, 2017

(30) Foreign Application Priority Data

Sep. 9, 2015 (JP) .................................. 2015-177632

(51) Int. Cl.
G01N 33/00 (2006.01)
G01N 27/12 (2006.01)

(52) U.S. Cl.
CPC ....... G01N 33/0036 (2013.01); G01N 27/121 (2013.01); G01N 33/0009 (2013.01)

(58) Field of Classification Search
CPC ................................................. G01N 33/0036
See application file for complete search history.

(56) References Cited

U.S. PATENT DOCUMENTS

| 2011/0138904 | A1* | 6/2011 | Nakaso ................ G01N 29/022 73/203 |
| 2013/0008240 | A1 | 1/2013 | Ito et al. |
| 2013/0323407 | A1* | 12/2013 | Wurzinger .......... C23C 16/4485 427/10 |
| 2014/0117824 | A1* | 5/2014 | Hayami .................... B01L 7/00 312/236 |

FOREIGN PATENT DOCUMENTS

| CN | 103427496 A | 12/2013 |
| CN | 103597065 A | 2/2014 |
| JP | H 08-261893 A | 10/1996 |
| JP | 2010-60452 | 3/2010 |
| JP | 2011-106894 | 6/2011 |
| JP | 2011-179975 | 9/2011 |
| JP | 2013-249538 A | 12/2013 |

OTHER PUBLICATIONS

Power by PROXI website archive. Jul. 4, 2014. https://web.archive.org/web/20140704130628/http://powerbyproxi.com/wireless-power/.*

* cited by examiner

*Primary Examiner* — Paul M. West
*Assistant Examiner* — Mark A Shabman
(74) *Attorney, Agent, or Firm* — Oblon, McClelland, Maier & Neustadt, L.L.P.

(57) ABSTRACT

A gas detection device includes: a gas sensor that detects a gas based on a change in an electric signal due to adsorption of a gas to be measured; a rotary body having the gas sensor mounted therein; and a motor that rotates the rotary body. The gas sensor is disposed at a location apart from a rotation axis of the rotary body. The motor rotates the rotary body at a constant rate.

6 Claims, 5 Drawing Sheets

GAS DETECTION DEVICE

CROSS-REFERENCE TO RELATED APPLICATIONS

This application is based upon and claims the benefit of priority from Japanese patent application No. 2015-177632, filed on Sep. 9, 2015, the disclosure of which is incorporated herein in its entirety by reference.

BACKGROUND OF THE INVENTION

1. Field of the Invention

The present invention relates to a gas detection device.

2. Description of Related Art

For example, an all-solid-state battery, such as a lithium-ion battery, has a structure in which stacked electrodes are sealed with a laminated film. In this case, if the material of the all-solid-state battery reacts with moisture in the air, the battery performance is significantly lowered. For this reason, it is necessary to secure the sealing quality of the laminated film.

However, since the all-solid-state battery is encapsulated by decompressing the inside of the laminated film, it is difficult to detect a leak gas from the outside of the laminated film to secure the sealing quality of the laminated film. For this reason, it is necessary to dispose a gas sensor at the inside of the laminated film, or in an enclosed space, to detect moisture (water vapor).

Japanese Unexamined Patent Application Publication No. 2011-106894 discloses a method for measuring a gas concentration by a quartz resonator sensor disposed in an enclosed space.

However, in the gas sensor, such as the quartz resonator sensor disclosed in Japanese Unexamined Patent Application Publication No. 2011-106894, which detects a gas according to a change in an electrical signal due to adsorption of a gas to be measured, the response speed and the detection sensitivity are greatly influenced by the flow rate of the gas to be measured. In particular, as the flow rate of the gas decreases, the response speed and the detection sensitivity decrease. Accordingly, there is a problem that it is difficult to detect a gas remaining in, for example, an enclosed space, with high accuracy.

SUMMARY OF THE INVENTION

It is an object of the present invention to provide a gas detection device capable of detecting a gas with high accuracy even in a state where a gas to be measured is stagnant.

A first exemplary aspect of the present invention is a gas detection device including: a gas sensor that detects a gas based on a change in an electric signal due to adsorption of a gas to be measured; a rotary body having the gas sensor mounted therein; and a drive unit that rotates the rotary body. The gas sensor is disposed at a location apart from a rotation axis of the rotary body, and the drive unit rotates the rotary body at a constant rate.

The gas detection device according to the first exemplary aspect of the present invention can measure a gas in a state where the flow rate of the stagnant gas is kept constant flow rate relative to the gas sensor, by revolving the gas sensor at a constant rate in a circle apart from the rotation axis. Accordingly, the gas can be detected with high accuracy.

The gas detection device according to the first exemplary aspect of the present invention further includes a sealed container that accommodates at least the gas sensor and the rotary body.

The gas detection device according to the first exemplary aspect of the present invention can measure a gas in a state where the flow rate of the stagnant gas is kept constant flow rate relative to the gas sensor, by revolving the gas sensor at a constant rate in a circle apart from the rotation axis. Accordingly, the stagnant gas in the sealed container can be detected with high accuracy.

In the gas detection device according to the first exemplary aspect of the present invention, the rotary body preferably includes a first magnet, and the drive unit preferably includes a second magnet. The drive unit preferably rotates the rotary body including the first magnet by causing the second magnet to rotate about the rotation axis, the first magnet and the second magnet attracting each other.

In the gas detection device according to the first exemplary aspect of the present invention, the drive unit and the rotary body include the magnets, respectively, at locations that are at the same distance from the rotation axis, thereby allowing the rotation of the drive unit to be transmitted to the rotary body in a non-contact manner.

The gas detection device according to the first exemplary aspect of the present invention preferably further includes: a power feeding unit that is disposed outside the sealed container and supplies AC power; a power feeding coil that is disposed outside the sealed container and generates a magnetic field by the AC power supplied from the power feeding unit; a power receiving coil that is disposed in the sealed container and generates AC power by the magnetic field generated by the power feeding coil; and an AC-DC conversion circuit that is disposed in the sealed container, converts the AC power into DC power, and supplies the DC power to the gas sensor. It is preferable that the power feeding coil and the power receiving coil have respective annular shapes with the same diameter and are disposed about the rotation axis of the rotary body.

In the gas detection device according to the first exemplary aspect of the present invention, the supply of power in a non-contact power transmission system makes it possible to supply power to the gas sensor and circuits, which are disposed in the enclosed space, detect a gas in the enclosed space, and measure a gas concentration.

The gas detection device according to the first exemplary aspect of the present invention preferably further includes: a transmission circuit that is disposed in the sealed container and converts data representing a gas concentration data measured by the gas sensor into a radio signal; a transmission antenna that is disposed in the sealed container and transmits the radio signal; a reception antenna that is disposed outside the sealed container and receives the radio signal; and a data conversion circuit that is disposed outside the sealed container and obtains the data representing the gas concentration from the radio signal. It is preferable that the transmission antenna and the reception antenna have respective annular shapes with the same diameter and are disposed about the rotation axis of the rotary body.

In the gas detection device according to the first exemplary aspect of the present invention, the data obtained by measuring the gas concentration is transmitted via the radio signal, thereby making it possible to transmit the result of measuring the gas concentration within the enclosed space to the outside.

The gas detection device according to the first exemplary aspect of the present invention can detect a gas with high accuracy even in a case where a gas to be measured is stagnant.

The above and other objects, features and advantages of the present invention will become more fully understood

DESCRIPTION OF THE EXEMPLARY EMBODIMENTS

First Exemplary Embodiment

Figure 1:
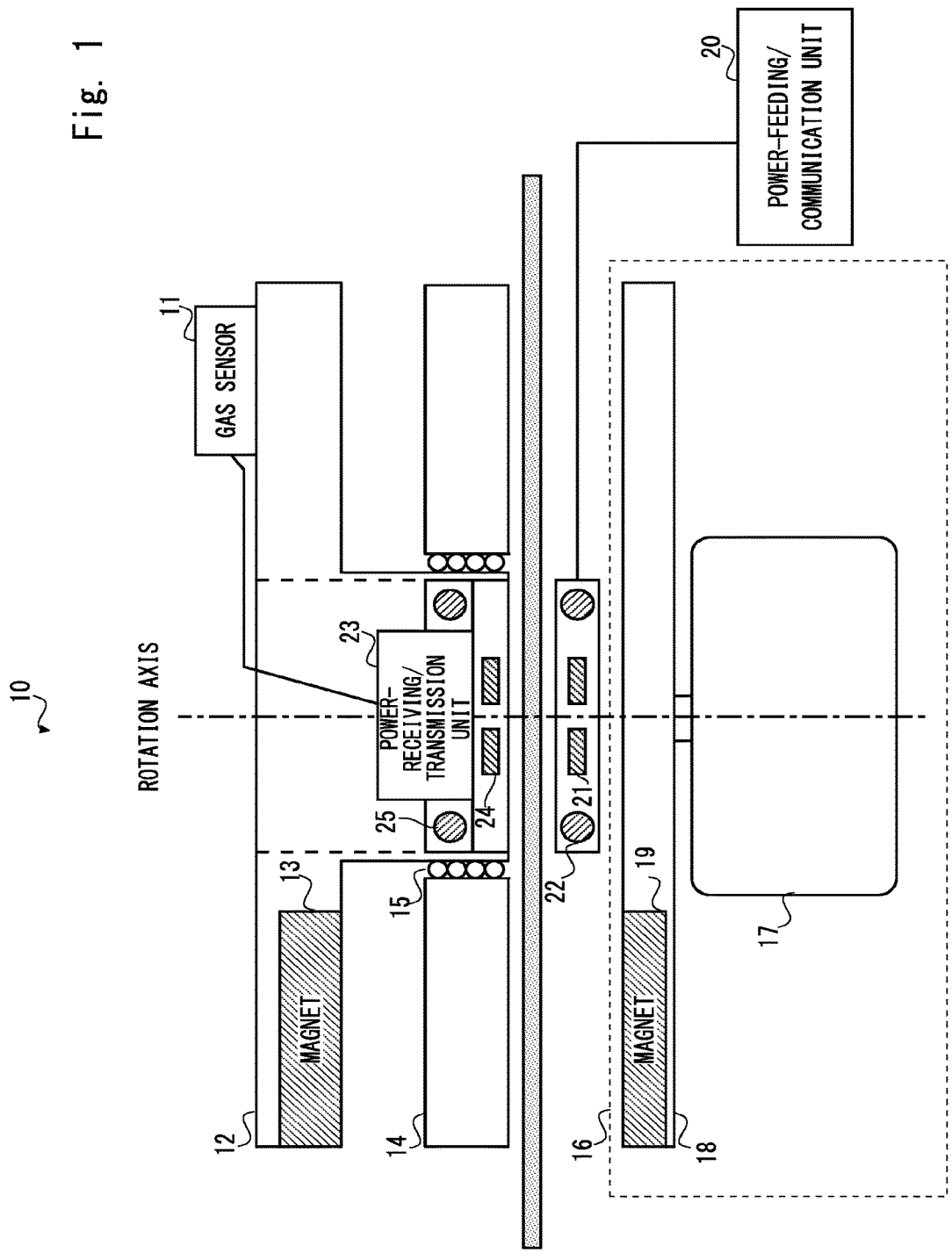
FIG. 1 is a sectional view showing a configuration of a gas detection device according to a first exemplary embodiment

Exemplary embodiments of the present invention will be described below with reference to the drawings. FIG. 1 is a sectional view showing a configuration of a gas detection device according to a first exemplary embodiment.

Referring to FIG. 1, a gas detection device 10 includes a gas sensor 11, a rotary body 12, a first magnet 13, a fixing base 14, a bearing 15, a motor 17, a rotor plate 18, a second magnet 19, a power-feeding/communication unit 20, a power feeding coil 21, a reception antenna 22, a power-receiving/transmission unit 23, a power receiving coil 24, and a transmission antenna 25.

The gas sensor 11 detects a gas by measuring a change in an electric signal due to adsorption of a gas to be measured. For example, a spherical SAW sensor or a planar SAW sensor is preferably used as the gas sensor 11. The spherical SAW sensor can measure a gas concentration based on a propagation time of an elastic surface wave which repeatedly revolves around the surface of a sphere. A gas component to be detected by the gas sensor 11 differs depending on the type of the sensor. For example, the spherical SAW sensor is capable of detecting moisture (water vapor) and measuring the concentration of the moisture.

The rotary body 12 has the gas sensor 11 mounted therein. The gas sensor 11 is mounted at a location apart from the rotation axis of the rotary body 12. The rotary body 12 includes the first magnet 13 which is disposed at a location apart from the rotation axis of the rotary body. The rotary body 12 is rotated in synchronization with the rotation of the rotor plate 18 including the second magnet 19.

The rotary body 12 also includes the power-receiving/transmission unit 23, the power receiving coil 24, and the transmission antenna 25. For example, the rotary body 12 desirably has a configuration in which a hollow is formed in the vicinity of the rotation axis, and the power-receiving/transmission unit 23, the power receiving coil 24, and the transmission antenna 25 are disposed in the hollow in the vicinity of the rotation axis of the rotary body 12. The power feeding coil 21 and the reception antenna 22, which are described later, are also disposed in the vicinity of the rotation axis of the rotary body. With this configuration, the power receiving coil 24 and the power feeding coil 21 can be kept in their respective locations when the rotary body 12 is rotated. Similarly, the transmission antenna 25 and the reception antenna 22 can be kept in their respective locations when the rotary body 12 is rotated.

For example, the rotary body 12 may have a shape obtained by combining a disc and a hollow cylinder. The gas sensor 22 is disposed on the entire surface of the disc. The first magnet 13 is disposed in the disc, and the power-receiving/transmission unit 23 is disposed in the hollow of the cylinder. Resin is preferably used as the material of the rotary body 12.

The fixing base 14 is a support member that supports the rotary body 12 through the bearing 15. For example, the fixing base 14 has a cylindrical hole formed at the center of the disc, and rotatably supports the rotary body 12 through the bearing 15.

The bearing 15 is a rolling bearing that is located between the rotary body 12 and the fixing base 14, and is in contact with each of the rotary body 12 and the fixing base 14. For example, a ball bearing is preferably used as the bearing 15.

A drive unit 16 includes the motor 17, the rotor plate 18, and the second magnet 19. The drive unit 16 rotates the rotary body 12. The details of a rotation method will be described later.

The rotating shaft of the motor 17 is connected to the rotor plate 18, and rotates the rotor plate 18. Any motor may be used as the motor 17 as long as the motor can be rotated at a constant rate. For example, a brushless motor that controls a rotational speed by feeding back the rotational speed is preferably used.

The rotor plate 18 includes the second magnet 19 disposed at a location apart from the rotation axis of the rotor plate. The first magnet 13 and the second magnet 19 are opposed to each other with different polarities, thereby generating an attracting force. For example, the first magnet 13 and the second magnet 19 are disposed in such a manner that the N-pole of the first magnet 13 and the S-pole of the second magnet 19 are opposed to each other.

Figure 2:
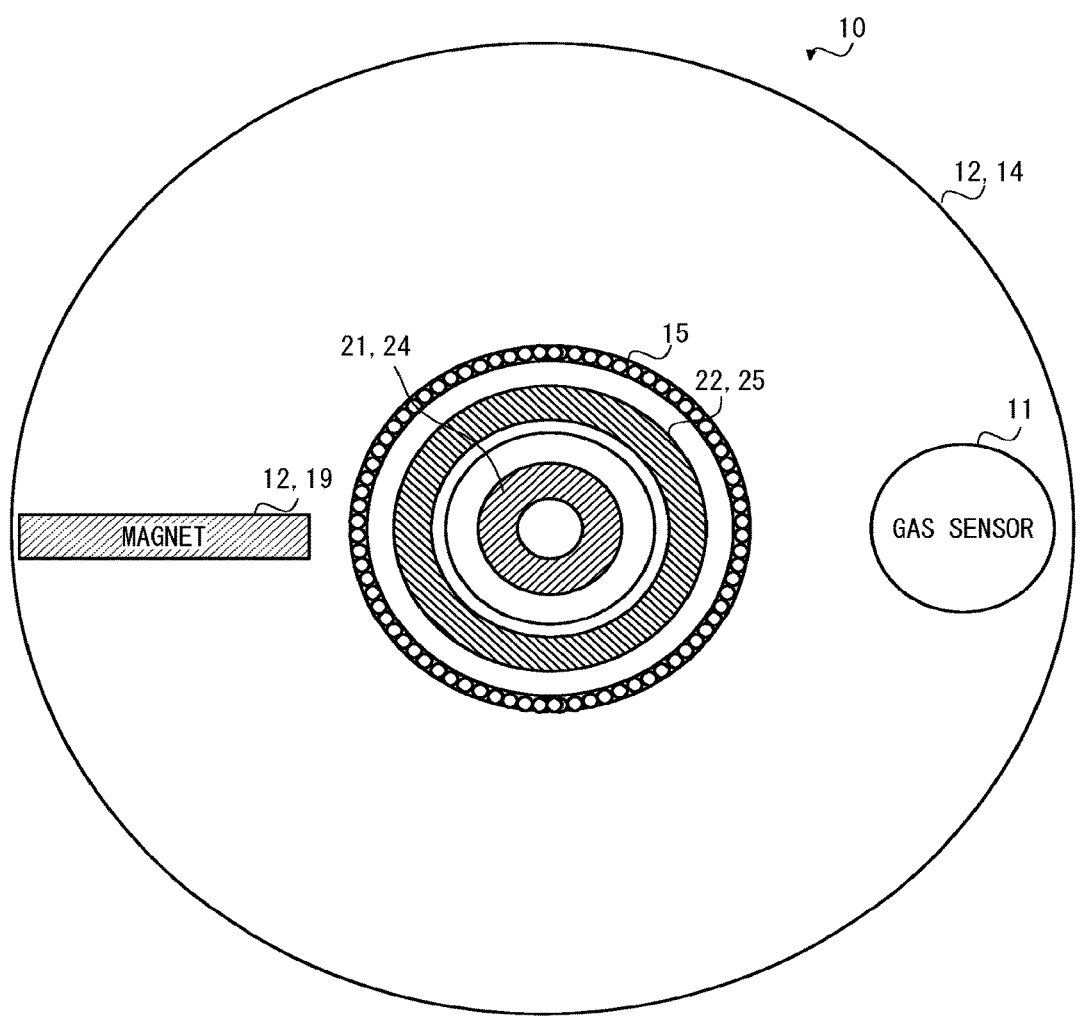
FIG. 2 is a top perspective view showing the configuration of the gas detection device according to the first exemplary embodiment.

The arrangement of these components viewed along the rotation axis direction will be described with reference to FIG. 2. FIG. 2 is a top perspective view showing the configuration of the gas detection device according to the first exemplary embodiment. As shown in FIG. 2, the rotary body 12, the fixing base 14, the rotor plate 18, and the motor 17 are disposed in such a manner that they have the same rotation axis (center axis).

The first magnet 13 and the second magnet 19 are disposed at locations that are at the same distance from the rotation axis. Accordingly, when the motor 17 is rotated, the second magnet 19 is revolved with a predetermined radius of rotation. The first magnet 13 is revolved at a predetermined radius of rotation in synchronization with the second magnet 19. The first magnet 13 and the second magnet 19 attract each other. Since the first magnet 13 is fixed to the rotary body 12 at a location apart from the rotation axis, the rotary body 12 is rotated when the first magnet 13 is revolved.

The gas sensor 11 is disposed on the rotary body 12 at a location apart from the rotation axis. Accordingly, the gas sensor 11 is revolved in accordance with the rotation of the rotary body 12. In the example shown in the figure, the gas sensor 11 is fixed to a peripheral portion of the rotary body 12. As the location where the gas sensor 11 is fixed is kept away from the rotation axis in the radial direction, that is, as the gas sensor 11 is fixed at a location closer to the peripheral portion of the rotary body, the traveling speed of the gas sensor 11 can be increased even if the rotation rate of the rotary body 12 is not changed. Furthermore, the fixation of the gas sensor 11 to the peripheral portion of the rotary body 12 leads to miniaturization (reduction in diameter) of the rotary body 12.

Since the motor 17 is rotated at a constant rate, the gas sensor 11 is also revolved at a constant rate. That is, the flow rate of surrounding gas is kept constant flow rate relative to the gas sensor 11. In other words, the surrounding gas flows at a constant flow rate relative to the gas sensor 11.

Thus, in the gas detection device according to the first exemplary embodiment, the gas sensor is revolved at a constant rate, thereby making it possible to detect a gas in a state where the flow rate of surrounding gas is kept at a constant flow rate relative to the gas sensor. Accordingly, even in a state where a gas to be measured is stagnant, the gas can be detected with high accuracy and the concentration of the gas can be measured with high accuracy.

The gas detection device according to the first exemplary embodiment is suitable for detecting a gas within the sealed container, but the present invention is not limited to this.

According to the gas detection device of the first exemplary embodiment, the drive unit and the rotary body include the magnets, respectively, at locations at the same distance from the rotation axis, thereby allowing the rotation of the drive unit to be transmitted to the rotary body in a non-contact manner.

Referring again to FIG. 1, the components related to the supply of power and the transmission of measurement data will be described below.

The power-feeding/communication unit 20 is electrically connected to the power feeding coil 21 and the reception antenna 22. The power-feeding/communication unit 20 causes an alternating current to flow through the power feeding coil 21. Further, the power-feeding/communication unit 20 amplifies and converts a radio signal received by the reception antenna 22, to thereby obtain digital data representing the gas concentration.

The power feeding coil 21 converts the alternating current output from the power-feeding/communication unit 20 into a magnetic field. For example, the power feeding coil 21 is preferably formed of one or more annular metallic wires.

The reception antenna 22 receives radio data transmitted from the transmission antenna 25, and outputs the received radio data to the power-feeding/communication unit 20.

The power-receiving/transmission unit 23 is electrically connected to the power receiving coil 24, the transmission antenna 25, and the gas sensor 11. The power-receiving/transmission unit 23 uses the alternating current output from the power receiving coil 24 as the power for the power-receiving/transmission unit 23 and the gas sensor 11. Further, the power-receiving/transmission unit 23 converts measurement data output from the gas sensor 11 into a radio signal, and outputs the radio signal to the transmission antenna 25.

The power receiving coil 24 converts the magnetic field, which is generated by the power feeding coil 21, into an alternating current, and outputs the alternating current to the power-receiving/transmission unit 23.

The transmission antenna 25 transmits the radio signal to the reception antenna 22.

Figure 3:
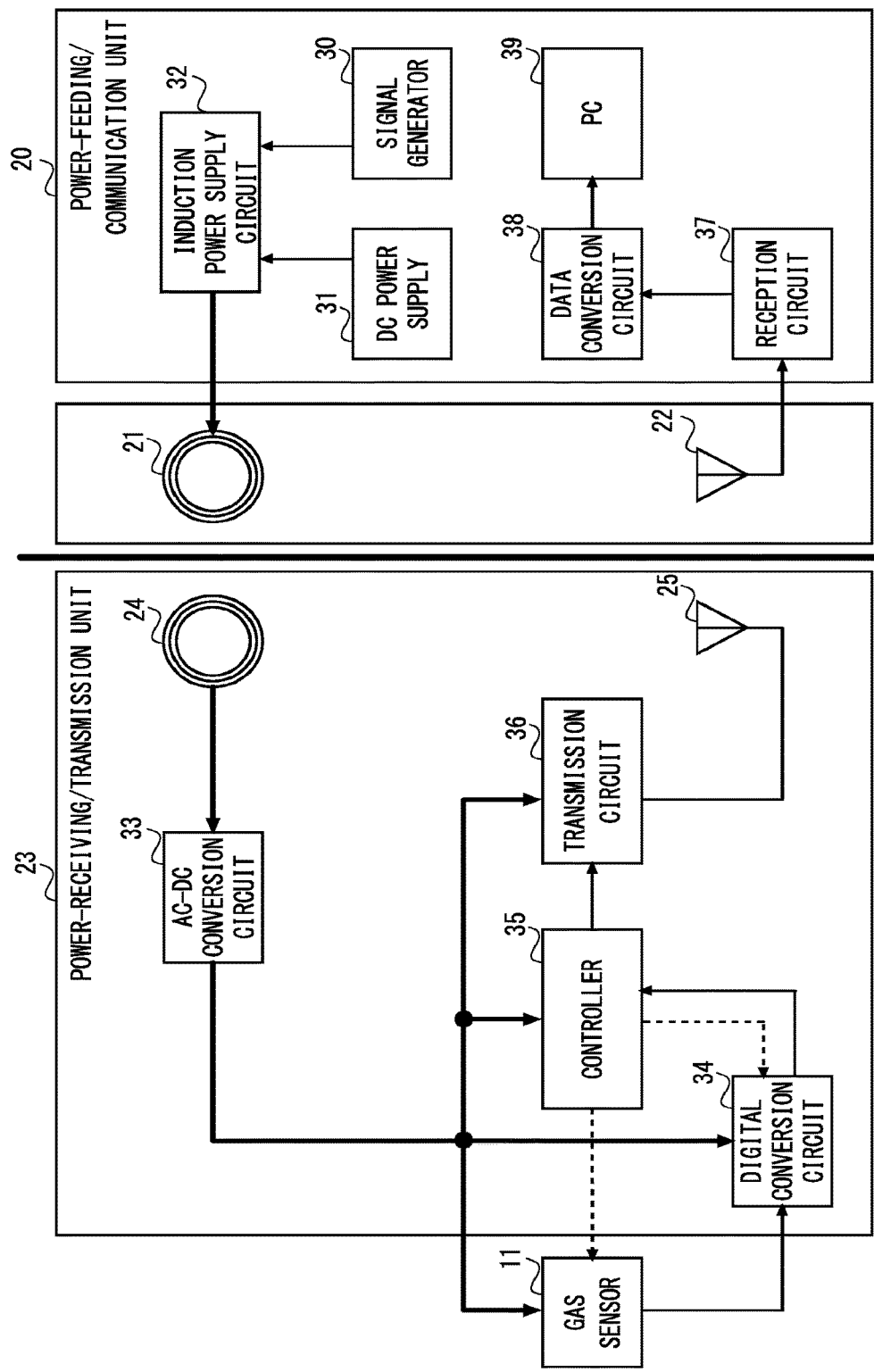
FIG. 3 is a block diagram showing electrical circuits of the gas detection device according to the first exemplary embodiment.

Details of the power-feeding/communication unit 20 and the power-receiving/transmission unit 23 will now be described. FIG. 3 is a block diagram showing electrical circuits of the gas detection device according to the first exemplary embodiment. In FIG. 3, a thick solid line represents a power line; a thin solid line represents a data line; and a broken line represents a control line. Referring to FIG. 3, the power-feeding/communication unit 20 includes a signal generator 30, a DC power supply 31, an induction power supply circuit 32, a reception circuit 37, a data conversion circuit 38, and a PC 39. The power-receiving/transmission unit 23 includes the power receiving coil 24, an AC-DC conversion circuit 33, a digital conversion circuit 34, a controller 35, a transmission circuit 36, and the transmission antenna 25. For example, the power-feeding/communication unit 20 and the power-receiving/transmission unit 23 are preferably formed of electronic circuit components or semiconductor circuits.

First, the configuration for supplying power from the power-feeding/communication unit 20 to the power-receiving/transmission unit 23 will be described.

The signal generator 30 generates an AC signal having a predetermined frequency, and outputs the generated AC signal to the induction power supply circuit 32.

The DC power supply 31 supplies a DC current to the induction power supply circuit 32.

The induction power supply circuit 32 supplies the power of the DC signal, which is supplied from the DC power supply 31, to the power feeding coil 21 as AC power having a frequency corresponding to the frequency of the AC signal output from the signal generator 30.

The power feeding coil 21 generates a magnetic field by the supplied AC power.

The power receiving coil 24 generates AC power by the magnetic field generated by the power feeding coil 21. In other words, the power receiving coil 24 is inductively coupled with the power feeding coil 21. Further, the power receiving coil 24 supplies the AC power to the AC-DC conversion circuit 33.

The AC-DC conversion circuit 33 converts the AC power into DC power. Further, the AC-DC conversion circuit 33 supplies the DC power to each of the digital conversion circuit 34, the controller 35, and the transmission circuit 36.

The non-contact power transmission using the configurations of the signal generator 30, the DC power supply 31, the induction power supply circuit 32, the power feeding coil 21, the power receiving coil 24, and the AC-DC conversion circuit 33 makes it possible to supply power to each of the digital conversion circuit 34, the controller 35, and the transmission circuit 36 in a state where the power-feeding/communication unit 20 and the power-receiving/transmission unit 23 are not in contact with each other.

Not only an electromagnetic induction system, but also a magnetic resonance system can be used as the non-contact power transmission system.

Next, the configuration for transmitting the measurement result of the gas sensor 11 from the power-receiving/transmission unit 23 to the power-feeding/communication unit 20 will be described.

The gas sensor 11 measures a change in an electric signal due to adsorption of the gas to be measured. Further, the gas sensor 11 outputs analog data representing the measured gas concentration to the digital conversion circuit 34.

The digital conversion circuit 34 amplifies the analog data representing the measured gas concentration, and converts the analog data into digital data, thereby obtaining the digital data. Further, the digital conversion circuit 34 outputs the digital data representing the measured gas concentration to the controller 35.

The controller 35 encodes the digital data representing the measured gas concentration. Further, the controller 35 outputs the encoded digital data to the transmission circuit 36. As indicated by a broken-line arrow in FIG. 3, the controller 35 controls the gas sensor 11 and the digital conversion circuit 34. For example, the controller 35 controls the conditions for measurement by the gas sensor 11, amplification factors for the digital conversion circuit 34, and the like.

The transmission circuit 36 performs modulation, frequency conversion, and amplification of the digital data representing the gas concentration, to thereby obtain a modulated wave. Further, the transmission circuit 36 outputs the modulated wave to the transmission antenna 25.

The transmission antenna 25 transmits the modulated wave as a radio wave.

The reception antenna 22 receives the radio wave and obtains the modulated wave. Further, the reception antenna 22 outputs the modulated wave to the reception circuit 37.

The reception circuit 37 performs amplification, frequency conversion, and demodulation of the modulated wave, to thereby obtain the digital data. Further, the reception circuit 37 outputs the digital data to the data conversion circuit 38.

The data conversion circuit 38 decodes the digital data. Further, the data conversion circuit 38 outputs the decoded digital data to the PC 39. The decoded digital data includes the digital data representing the gas concentration.

The PC 39 stores and displays the digital data representing the gas concentration.

With the above-described configuration, power is supplied from the power-receiving/transmission unit 23 to the power-feeding/communication unit 20, and the data representing the gas concentration measured by the gas sensor 11 is transmitted from the power-receiving/transmission unit 23 to the power-feeding/communication unit 20.

The supply of power and the transmission of data representing the measured gas concentration are performed between the rotating power-receiving/transmission unit 23 and the non-rotating power-feeding/communication unit 20. Accordingly, it is necessary to take into consideration the shape and layout of the coils and antennas of the rotating power-receiving/transmission unit 23 and the non-rotating power-feeding/communication unit 20. Referring again to FIG. 2, the shape and layout of the power feeding coil 21, the power receiving coil 24, the transmission antenna 25, and the reception antenna 22 will be described below.

As shown in FIG. 2, the power feeding coil 21 and the power receiving coil 24 are disposed in an overlapping manner, when viewed along the rotation axis direction, so that they are centered on the rotation axis. Further, since the power feeding coil 21 and the power receiving coil 24 have respective annular shapes with the same diameter, the relative locations of the power feeding coil 21 and the power receiving coil 24 do not change even when the rotary body 12 is rotated. In other words, during the rotation of the rotary body 12, a stable inductive coupling between the power feeding coil 21 and the power receiving coil 24 is obtained, which enables supply of power from the power-feeding/communication unit 20 to the power-receiving/transmission unit 23 in a non-contact manner.

The transmission antenna 25 and the reception antenna 22 are also disposed in an overlapping manner in a plane of projection from the rotation axis direction. Further, since the transmission antenna 25 and the reception antenna 22 have respective annular shapes with the same diameter, the relative locations of the transmission antenna 25 and the reception antenna 22 do not change even when the rotary body 12 is rotated. Accordingly, during the rotation of the rotary body 12, data can be stably transmitted from the transmission antenna 25 to the reception antenna 22.

Thus, according to the gas detection device of the first exemplary embodiment, the supply of power in the non-contact power transmission system makes it possible to supply power to the gas sensor and circuits, which are disposed in the enclosed space, and to measure the concentration of the gas within the enclosed space.

Furthermore, according to the gas detection device of the first exemplary embodiment, the data representing the measured gas concentration is transmitted via the radio signal, so that the result of measuring the concentration of the gas within the enclosed space can be transmitted to the outside.

Second Exemplary Embodiment

Figure 4:
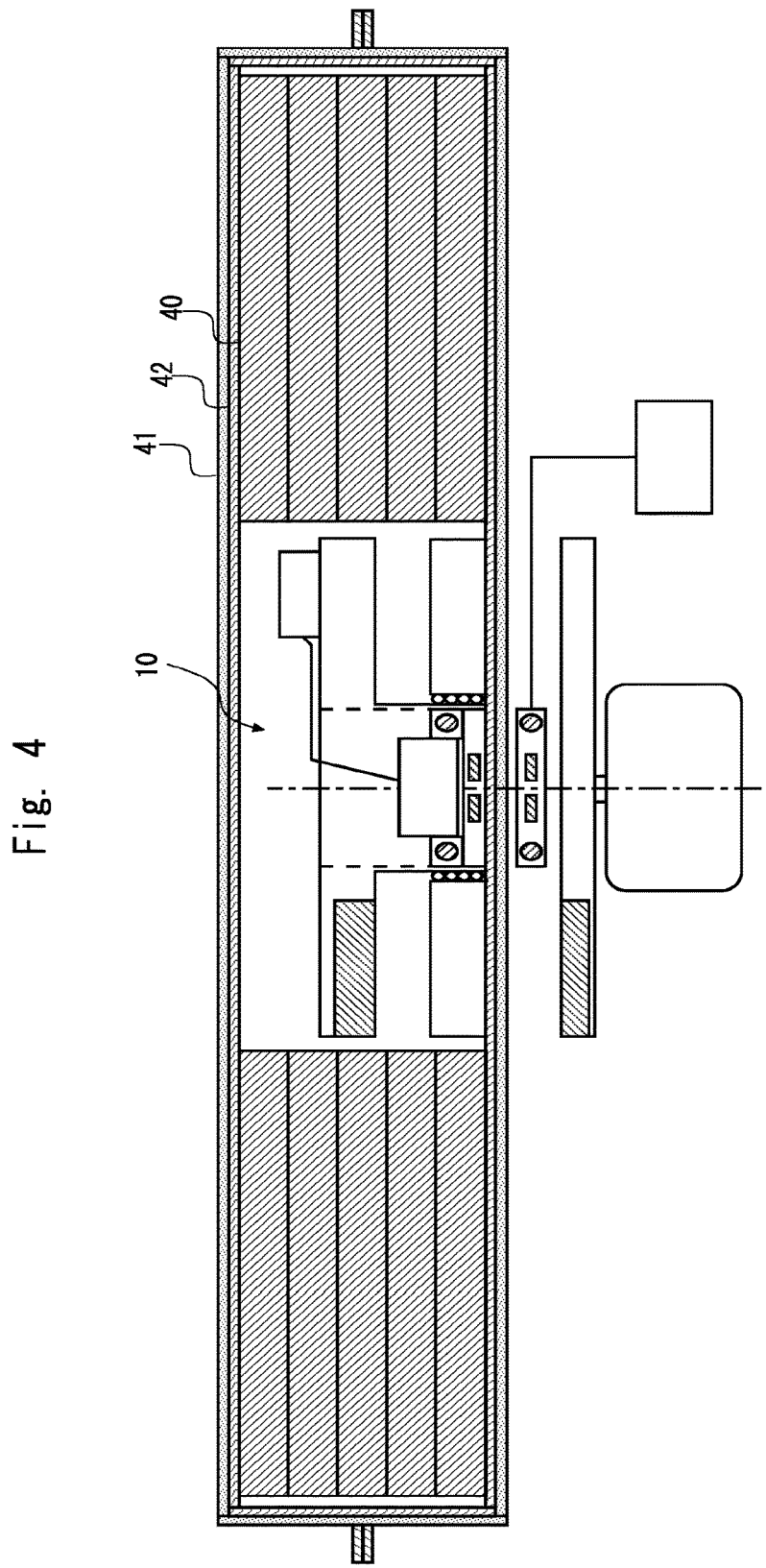
FIG. 4 is a sectional view showing configurations of a gas detection device and a lithium-ion battery according to a second exemplary embodiment.

In a second exemplary embodiment, a method for evaluating the sealing quality of the sealed container of a stacked body 40 by using the gas detection device 10 of the first exemplary embodiment is described. In the case of measuring the concentration of the gas within the sealed container, at least the gas sensor 11 and the rotary body 12 are disposed in the sealed container. FIG. 4 is a sectional view showing configurations of the gas detection device and a lithium-ion battery according to the second exemplary embodiment.

As shown in FIG. 4, the gas detection device 10 and the stacked body 40 of the lithium-ion battery are disposed in a sealed container 41.

The sealed container 41 is a sealed container that covers the gas detection device 10 and the stacked body 40, to thereby form an enclosed space. The sealed container 41 is made of a material that allows a magnetic field to pass and does not allow moisture to pass. For example, a laminated film, especially, an aluminum laminated film, is preferably used for the sealed container 41.

A frame 42 is disposed in the sealed container 41, and has a configuration for preventing the sealed container 41 from being deformed due to decompression. In other words, the frame 42 prevents the sealed container 41 from being recessed due to decompression and interfering with the gas detection device 10. The frame 42 is made of a material that allows a magnetic field to pass and has rigidity necessary for preventing the frame 42 from being deformed due to decompression. Polyvinyl chloride is preferably used as the material of the frame 42.

The sealed container 41 and the frame 42 may have any shape as long as they can cover the gas detection device 10 and the stacked body 40. The frame 42 preferably has a lattice shape, a plate shape, or a combination thereof.

An electrode terminal of the stacked body 40 is sandwiched between laminated films to be welded, thereby establishing an electrical continuity with the outside, while maintaining the sealed state.

A working load, such as, a vibration (external force), a temperature, or charging/discharging, is applied to the sealed container 41 in which the stacked body 40 is enclosed as described above, and the sealing quality of the sealed container is evaluated. For example, a vibration is applied by a vibrator. The temperature can be increased by a heat source. Charging/discharging is carried out by a charging/discharging device.

Thus, according to the sealing quality evaluation method of the second exemplary embodiment, the gas sensor is revolved at a constant rate in a circle apart from the rotation axis, thereby making it possible to measure the stagnant gas in a state where the flow rate of the stagnant gas is kept constant flow rate relative to the gas sensor. Therefore, the stagnant gas in the sealed container can be detected with high accuracy and the sealing quality of the sealed container can be evaluated with high accuracy.

The present invention is not limited to the above exemplary embodiments, and can be modified as appropriate without departing from the scope of the invention.

Figure 5:
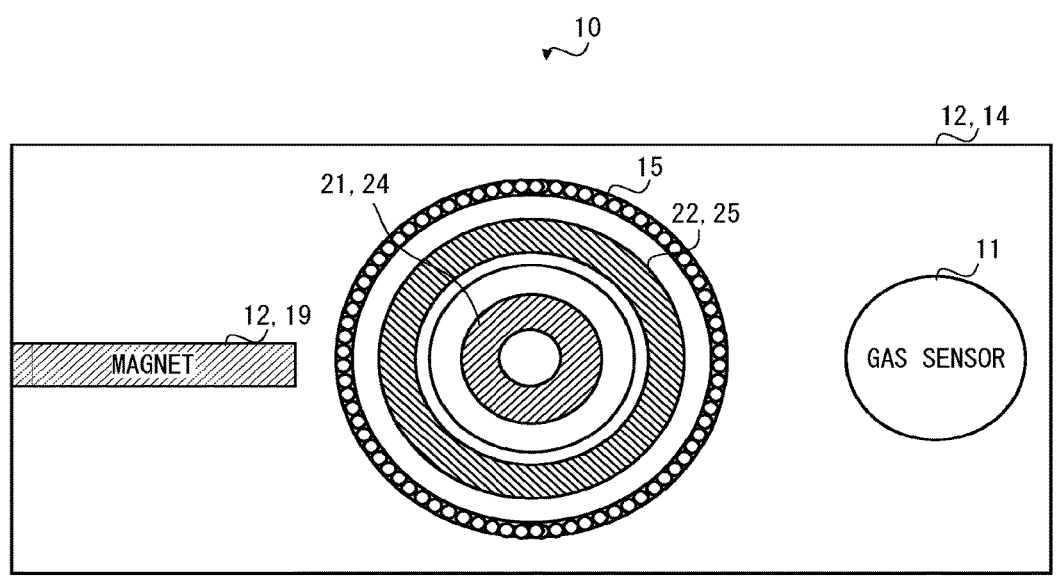
FIG. 5 is a top perspective view showing a configuration of a modified example of the gas detection device according to the first exemplary embodiment.

For example, in the above exemplary embodiments, the motor 17 is disposed outside the sealed container. However, the motor 17 may be disposed in the sealed container and may be supplied through a radio wave from the outside of the sealed container. The rotary body 12 and the rotor plate 18 may have any shape other than a disc shape, as long as the gas sensor 11 can be disposed at a location apart from the rotation axis. FIG. 5 is a top perspective view showing a configuration of a modified example of the gas detection device according to the first exemplary embodiment. For example, as shown in FIG. 5, the rotary body 12 may have a square bar shape, instead of a disc shape, and the gas sensor 11 may be disposed on the square bar, or at an end of the square bar, at a location apart from the rotation axis. The rotor plate may also have a square bar shape, instead of a disc shape.

The rotation axis of the rotary body 12 desirably corresponds to the center of mass thereof. Accordingly, the rotary body 12 desirably includes a counterweight when the center of mass of the rotary body 12 is deviated from the rotation axis by the gas sensor 11 or the magnet.

Permanent magnets are preferably used as the first magnet 13 and the second magnet 19. However, electromagnets may also be used as the first magnet and the second magnet. In this case, it is desirable to generate a magnetic force by supplying power to the first magnet 13 in the non-contact power transmission system, like in the gas sensor 11. The first magnet 13 may be disposed in the rotary body 12, or may be disposed on the surface thereof. Similarly, the second magnet 19 may be disposed in the rotor plate 18, or may be disposed on the surface thereof.

The gas sensor 11 can be disposed at any location on the rotary body 12, as long as the location is apart from the rotation axis of the rotary body 12 and is accessible to the gas.

Any gas sensor can be used as the gas sensor 11, as long as the gas sensor can measure a change in an electric signal due to adsorption of the gas to be measured. For example, an electrical capacitance gas sensor that measures a change in capacitance due to adsorption of a gas, and a semiconductor gas sensor that measures a change in resistance value due to adsorption of a gas can also be used. The gas sensor 11 may detect a gas component.

In the above exemplary embodiments, the rotary body 12 and the rotor plate 18 are rotated in synchronization with each other by a magnetic force. Alternatively, the motor 17 may be disposed in the enclosed space and the rotary body 12 may be rotated by the motor 17. In this case, the motor 17 is desirably supplied with power from a battery or by non-contact power transmission.

In the above embodiments, the measured data is transmitted using a radio signal, and the data is stored and displayed on the PC 39 which is located outside the sealed container. Alternatively, a small logger may be disposed in the sealed container, and the measured data may be stored in the logger.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A gas detection device comprising:
   a gas sensor that measures a gas concentration based on a change in an electric signal due to adsorption of a gas to be measured;
   a rotary body having the gas sensor mounted therein; and
   a drive unit that rotates the rotary body, wherein
   the gas sensor is disposed at a location apart from a rotation axis of the rotary body, and
   the drive unit rotates the rotary body at a constant rate.

2. The gas detection device according to claim 1, further comprising a sealed container that accommodates at least the gas sensor and the rotary body.

3. The gas detection device according to claim 2, further comprising:
   a power feeding unit that is disposed outside the sealed container and supplies AC power;
   a power feeding coil that is disposed outside the sealed container and generates a magnetic field by the AC power supplied from the power feeding unit;
   a power receiving coil that is disposed in the sealed container and generates AC power by the magnetic field generated by the power feeding coil; and
   an AC-DC conversion circuit that is disposed in the sealed container, converts the AC power into DC power, and supplies the DC power to the gas sensor,
   wherein the power feeding coil and the power receiving coil have respective annular shapes with the same diameter, and are disposed about the rotation axis of the rotary body.

4. The gas detection device according to claim 2, further comprising:
   a transmission circuit that is disposed in the sealed container and converts data representing a gas concentration data measured by the gas sensor into a radio signal;
   a transmission antenna that is disposed in the sealed container and transmits the radio signal;
   a reception antenna that is disposed outside the sealed container and receives the radio signal; and
   a data conversion circuit that is disposed outside the sealed container and obtains the data representing the gas concentration from the radio signal,
   wherein the transmission antenna and the reception antenna have respective annular shapes with the same diameter and are disposed about the rotation axis of the rotary body.

5. The gas detection device according to claim 2, wherein the gas sensor is fixed to a peripheral portion of the rotary body.

6. The gas detection device according to claim 1, wherein the rotary body includes a first magnet, and the drive unit includes a second magnet, and
   the drive unit rotates the rotary body including the first magnet by causing the second magnet to rotate about the rotation axis, the first magnet and the second magnet attracting each other.

* * * * *